US011363391B2

United States Patent
El Guindi et al.

(10) Patent No.: US 11,363,391 B2
(45) Date of Patent: Jun. 14, 2022

(54) SYSTEMS AND METHODS FOR BIOMARKER ANALYSIS ON A HEARING DEVICE

(71) Applicant: SONOVA AG, Staefa (CH)

(72) Inventors: Nadim El Guindi, Zürich (CH); Anne Thielen, Stäfa (CH)

(73) Assignee: Sonova AG, Staefa (CH)

(*) Notice: Subject to any disclaimer, the term of this patent is extended or adjusted under 35 U.S.C. 154(b) by 156 days.

(21) Appl. No.: 16/828,695

(22) Filed: Mar. 24, 2020

(65) Prior Publication Data
US 2021/0306770 A1 Sep. 30, 2021

(51) Int. Cl.
| G08B 21/04 | (2006.01) |
| H04R 25/00 | (2006.01) |
| H04M 1/72412 | (2021.01) |
| H04M 1/72454 | (2021.01) |
| A61B 5/00 | (2006.01) |

(52) U.S. Cl.
CPC ......... *H04R 25/505* (2013.01); *A61B 5/4803* (2013.01); *A61B 5/7282* (2013.01); *H04M 1/72412* (2021.01); *H04M 1/72454* (2021.01); *H04R 25/554* (2013.01); *H04R 25/606* (2013.01); *A61B 5/4082* (2013.01); *A61B 5/4088* (2013.01); *H04R 2225/43* (2013.01); *H04R 2460/13* (2013.01)

(58) Field of Classification Search
CPC ......... G10L 25/90; G10L 25/87; G10L 25/63; G10L 25/51; G10L 25/66
See application file for complete search history.

(56) References Cited

U.S. PATENT DOCUMENTS

| 5,754,665 A | * | 5/1998 | Hosoi | H04R 3/005 381/92 |
| 10,045,321 B2 | | 8/2018 | Goldstein | |
| 2014/0114889 A1 | | 4/2014 | Dagum | |
| 2018/0125415 A1 | | 5/2018 | Reed | |
| 2020/0058208 A1 | * | 2/2020 | Ogaz | G10L 25/63 |

FOREIGN PATENT DOCUMENTS

| WO | 2017211426 | 12/2017 |
| WO | 2019075432 | 4/2019 |

OTHER PUBLICATIONS

Extended European Search Report received in EP Application No. 21155288.0-1207 dated Jul. 8, 2021.

* cited by examiner

*Primary Examiner* — Amir H Etesam
(74) *Attorney, Agent, or Firm* — ALG Intellectual Property, LLC

(57) ABSTRACT

An exemplary hearing device configured to be worn by a user includes a microphone and a processor. The microphone detects an audio signal. The processor is configured to determine that the audio signal includes own voice content representative of a voice of the user and determine that an environmental noise level within the audio signal is below a threshold The processor is further configured to apply, based on the environmental noise level being below the threshold, a biomarker feature analysis heuristic to the own voice content.

20 Claims, 5 Drawing Sheets

SYSTEMS AND METHODS FOR BIOMARKER ANALYSIS ON A HEARING DEVICE

BACKGROUND INFORMATION

Conventional diagnosis methods for neurodegenerative disorders are limited to perceptual tests or controlled laboratory setups. As such, such disorders are often diagnosed late, resulting in potentially serious conditions for those diagnosed with neurodegenerative disorders and high costs for treatment and care.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Exemplary systems and methods for biomarker analysis on a hearing device are described herein. For example, a hearing device may comprise a microphone configured to detect an audio signal and a processor communicatively coupled to the microphone. The processor may be configured to determine that the audio signal includes own voice content representative of a voice of the user and determine that an environmental noise level within the audio signal is below a threshold. The processor may be further configured to apply, based on the environmental noise level being below the threshold, a biomarker feature analysis heuristic to the own voice content.

The systems and methods described herein may advantageously provide many benefits to users of hearing devices. For example, the hearing devices described herein may analyze biomarker features extracted from the user's own voice to provide early detection of potential neurodegenerative disorders and/or other diseases of a user during a course of general usage by the user of the hearing device. This, in turn, may lead to earlier diagnosis and treatment of the neurodegenerative disorders and/or other diseases than conventional diagnosis methods. For at least these reasons, the systems and methods described herein may advantageously provide additional functionality and/or features for hearing device users compared to conventional hearing devices. These and other benefits of the systems and methods described herein will be made apparent herein.

Figure 1:
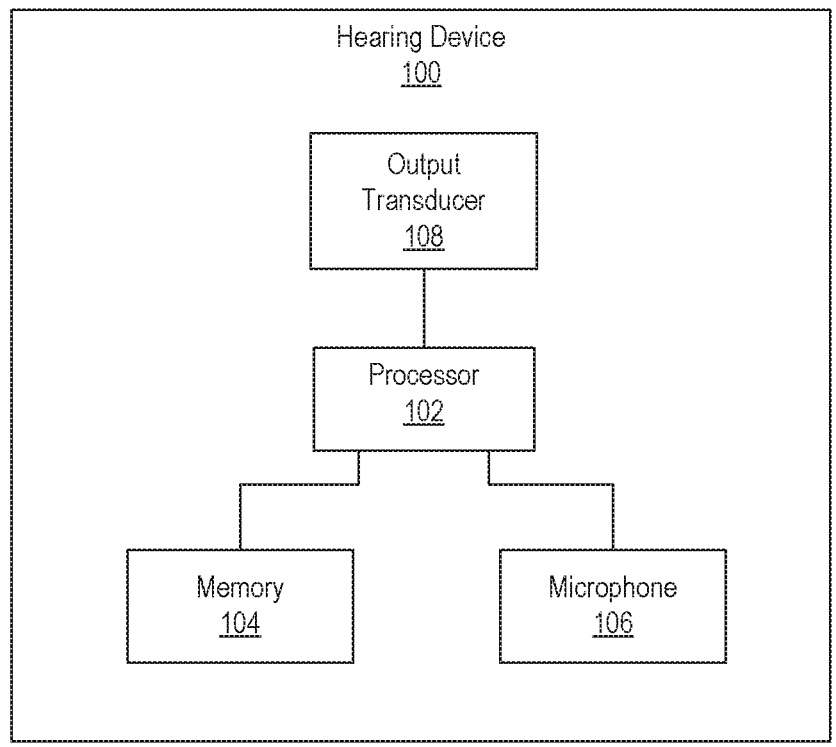
FIG. 1 illustrates an exemplary hearing device according to principles described herein.

FIG. 1 illustrates an exemplary hearing device 100. Hearing device 100 may be implemented by any type of hearing device configured to enable or enhance hearing by a user wearing hearing device 100. For example, hearing device 100 may be implemented by a hearing aid configured to provide an amplified version of audio content to a user, a sound processor included in a cochlear implant system configured to provide electrical stimulation representative of audio content to a user, a sound processor included in a bimodal hearing system configured to provide both amplification and electrical stimulation representative of audio content to a user, a head-worn headset, an ear-worn ear-bud, or any other suitable hearing prosthesis.

As shown, hearing device 100 includes a processor 102 communicatively coupled to a memory 104, a microphone 106, and an output transducer 108. Hearing device 100 may include additional or alternative components as may serve a particular implementation.

Microphone 106 may be implemented by any suitable audio detection device and is configured to detect an audio signal presented to a user of hearing device 100. The audio signal may include, for example, audio content (e.g., music, speech, noise, etc.) generated by one or more audio sources included in an environment of the user, including the user. Microphone 106 may be included in or communicatively coupled to hearing device 100 in any suitable manner. Output transducer 108 may be implemented by any suitable audio output device, for instance a loudspeaker of a hearing device or an output electrode of a cochlear implant system.

Memory 104 may be implemented by any suitable type of storage medium and may be configured to maintain (e.g., store) data generated, accessed, or otherwise used by processor 102. For example, memory 104 may maintain data representative of a plurality of sound processing programs that specify how processor 102 processes audio content (e.g., audio content included in the audio signal detected by microphone 106) to present the audio content to a user. To illustrate, if hearing device 100 is a hearing aid, memory 104 may maintain data representative of sound processing programs that specify audio amplification schemes (e.g., amplification levels, etc.) used by processor 102 to provide an amplified version of the audio content to the user. As another example, if hearing device 100 is a sound processor included in a cochlear implant system, memory 104 may maintain data representative of sound processing programs that specify stimulation schemes used by processor 102 to direct a cochlear implant to provide electrical stimulation representative of the audio content to the user.

Processor 102 may be configured to perform various processing operations with respect to an audio signal detected by microphone 106. For example, processor 102 may be configured to receive the audio signal (e.g., a digitized version of the audio signal) from microphone 106 and process the audio content contained in the audio signal in accordance with a biomarker feature analysis heuristic to detect early signs of neurodegenerative disease. These and other operations that may be performed by processor 102 are described in more detail herein. In the description that follows, any references to operations performed by hearing device 100 may be understood to be performed by processor 102 of hearing device 100. Processor 102 may be implemented by any suitable combination of hardware and software.

Figure 2:
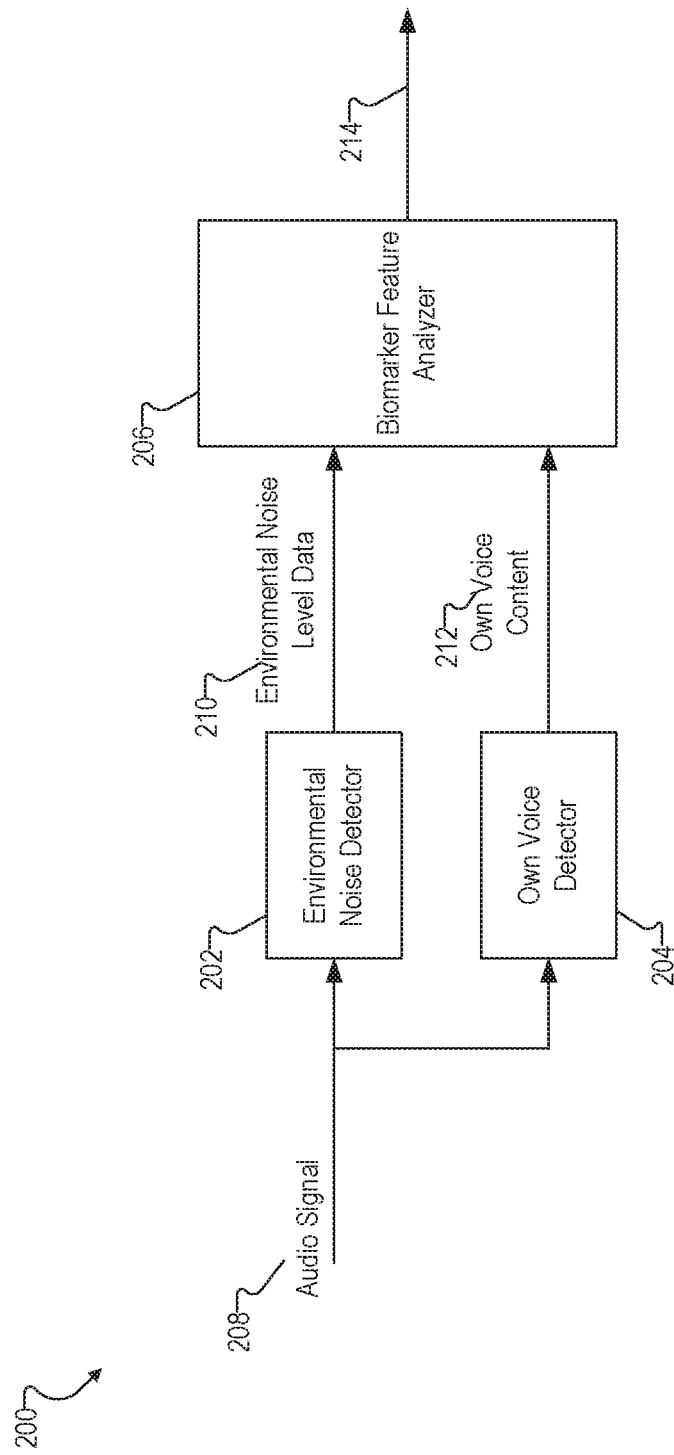
FIG. 2 illustrates an exemplary configuration for biomarker analysis according to principles described herein.

FIG. 2 illustrates an exemplary configuration 200 for biomarker analysis on a hearing device. Configuration 200 includes an environmental noise detector 202, an own voice detector 204, and a biomarker feature analyzer 206, each of which may be included in and/or communicatively coupled to a hearing device as described herein.

As shown, environmental noise detector 202 and own voice detector 204 may receive an audio signal 208 (e.g., a signal detected by a microphone of the hearing device, a signal transmitted to the hearing device by an audio source, etc.). Environmental noise detector 202 may detect an environmental noise component of audio signal 208. The environmental noise component may include data representative of environmental noise, which may include any audio present in an environment of a user of the hearing device, any audio detected by the hearing device from an environment of the user, and/or any audio excluding audio generated by the user. Environmental noise detector 202 may detect the environmental noise component in any suitable manner, examples of which are described herein. Environmental noise detector 202 may detect the environmental noise component and determine a level of the environmental noise. The level may be any suitable measurement of the environmental noise, such as a volume level, a relative volume level, a decibel level, an amplitude, a noise spectrum, a loudness level, etc. Environmental noise detector 202 may provide environmental noise level data 210 representative of the environmental noise level to biomarker feature analyzer 206.

Own voice detector 204 may receive audio signal 208 and detect an own voice component of audio signal 208. The own voice component may include data representative of own voice content 212 generated by a voice of the user. Own voice detector 204 may detect the own voice component in any suitable manner, examples of which are described herein. Own voice detector 204 may provide own voice content 212 to biomarker feature analyzer 206.

Biomarker feature analyzer 206 may receive environmental noise level data 210 and own voice content 212. Biomarker feature analyzer 206 may analyze own voice content 212 for biomarkers. Such analysis may be based on environmental noise level data 210. For example, biomarker feature analyzer 206 may determine whether environmental noise level data 210 indicates that the environmental noise level is below a threshold level so that own voice content 212 received may be clear enough for biomarker feature analysis. If the environmental noise level is too high (e.g., at or above the threshold level), own voice content 212 may include too much environmental noise for biomarker feature analyzer 206 to be able to accurately analyze for biomarkers.

Based on the environmental noise level being below the threshold, biomarker feature analyzer 206 may analyze own voice content 212 to extract biomarker features and analyze the biomarker features. Biomarker feature analyzer 206 may extract any suitable biomarker features and analyze the biomarker features for any suitable biological conditions of the user. Example biomarker features may include characteristics of respiration (e.g., relative loudness of respiration, latency of respiratory exchange, pause intervals per respiration, rate of speech respiration, etc.), characteristics of articulation (e.g., duration of unvoiced stops, decay of unvoiced fricatives, etc.), characteristics of timing (e.g., rate of speech timing, acceleration of speech timing, duration of pause intervals, entropy of speech timing, etc.), characteristics of phonation (e.g., gaping in-between voiced intervals, duration of voiced intervals, etc.), semantic content (e.g., a repetition of words by the user), and any other suitable characteristics. Such features may be analyzed for biological conditions such as neurodegenerative disorders (e.g., Parkinson's, Alzheimer's, etc.), or any other conditions that may be marked by speech and/or voice related biomarkers. Such analysis may also be performed using artificial intelligence techniques (e.g., deep learning, neural networks, etc.). Based on analysis of biomarker features, biomarker feature analyzer 206 may provide an output 214 indicating results of the biomarker feature analysis. As used herein, biomarker feature analysis heuristics may include extraction of biomarkers, biomarker features, and/or analysis of biomarker features for specific biological conditions.

Figure 3:
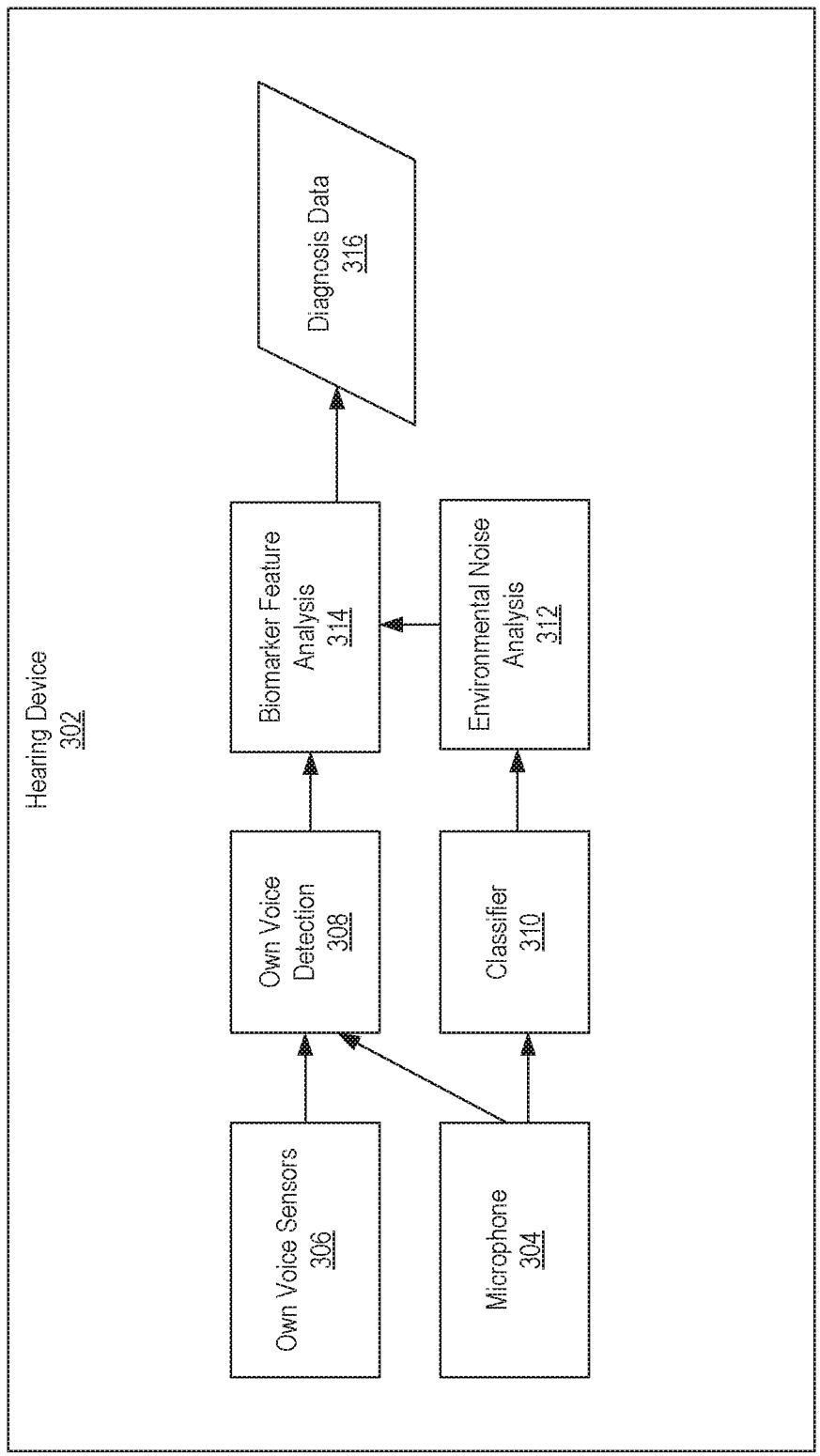
FIGS. 3-4 illustrate exemplary configurations of biomarker analysis on hearing devices according to principles described herein.

FIG. 3 illustrates an exemplary hearing device 302 configured to perform biomarker analysis. Hearing device 302 may be an implementation of hearing device 100 that includes an implementation of configuration 200. For instance, hearing device 302 includes a microphone 304 (e.g., an implementation of microphone 106) along with additional own voice sensors 306. Hearing device 302 further includes a classifier 310, an environmental noise analysis module 312, and a biomarker feature analysis module 314.

Own voice sensors 306 may be implemented in any suitable manner, using any sensors and/or devices capable of detecting a user's own voice content (e.g., detect audio content of the user's own voice) and/or providing information indicative of a presence of the user's own voice (e.g., an indication that the user is speaking). For example, own voice sensors 306 may include one or more of any combination of voice pickup sensors, microphones, bone conduction microphones, canal microphones, etc. In some alternative configurations, hearing device 302 does not include own voice sensors 306.

Own voice detection module 308 may receive data or any other suitable signal from microphone 304 and/or own voice sensors 306. Own voice detection module 308 may determine, based on the data received from microphone 304 and own voice sensors 306 whether own voice content is present in an audio signal detected by microphone 304. For example, own voice sensors 306 may provide information specifying portions (e.g., temporal portions) of the audio signal and/or times during which the user is speaking, which may indicate that the audio signal includes own voice content during those portions and/or times. Additionally or alternatively, own voice sensors 306 may provide data representative of the own voice content, such as from a localized and/or directional microphone configured to detect what the user is saying with minimal other audio content (e.g., environmental noise content).

In some examples, own voice detection module 308 may perform one or more algorithms to determine from the audio signal provided by microphone 304 whether the audio signal includes own voice content. For example, own voice detection module 308 may analyze a directionality and/or a volume level of the audio signal, store audio samples of the user's voice and perform voice and/or speech recognition algorithms on the audio signal, and/or use any other suitable techniques and algorithms for detecting own voice content in the audio signal. In some examples, hearing device 302 may include no own voice sensors 306 and own voice detection module 308 may detect own voice content based on such algorithms.

Classifier 310 may also receive the audio signal from microphone 304. Classifier 310 may be configured to classify a type of the audio content represented by the audio signal. For instance, classifier 310 may classify the audio content as music, speech, background noise, etc. Such classifications may provide additional information for analyzing an environmental noise component of the audio signal. In some examples, classifier 310 may analyze the audio signal to extract the own voice component and/or the environmental noise component from the audio signal. Classifier 310 may be implemented in any suitable manner. In some alternative implementations, hearing device 302 does not include classifier 310. In these alternative implementations, environmental noise analysis module 312 is configured to analyze the output of microphone 304 directly.

Environmental noise analysis module 312 may receive data from classifier 310, such as an environmental noise component of the audio signal. Additionally or alternatively, environmental noise analysis module 312 may receive the audio signal from classifier 310 (or from microphone 304) and analyze the audio signal for the environmental noise component of the audio signal. Based on the environmental noise component, environmental noise analysis module 312 may determine an environmental noise level. Environmental noise analysis module 312 may further determine whether the environmental noise level is above or below a threshold level that may allow for accurate biomarker feature analysis.

In some examples, environmental noise analysis module 312 may analyze the environmental noise component of the audio signal by analyzing one or more portions of the audio signal during which own voice content is absent (e.g., as determined by own voice detection module 308). Portions of the audio signal in which own voice content is determined to be absent may indicate that an entirety of the audio content represented by the audio signal during those portions is environmental noise. Thus, environmental noise analysis module 312 may analyze the environmental noise level during those portions of the audio signal.

Additionally or alternatively, environmental noise analysis module 312 may sample portions of the audio signal during which own voice content is absent. Environmental noise analysis module 312 may analyze such samples to determine whether the environmental noise is suitable for performing noise canceling techniques and/or algorithms. For instance, if the environmental noise is of a known type, the environmental noise is substantially periodic, the environmental noise has an unchanging or periodic average characteristic, and/or the environmental noise has other such suitable characteristics for canceling, environmental noise analysis module 312 may cancel the environmental noise. Such canceling may be to an extent that the canceled environmental noise is below the threshold for biomarker feature analysis.

Biomarker feature analysis module 314 may receive own voice content from own voice detection module 308 and environmental noise data from environmental noise analysis module 312. The own voice content may be included in portions of the audio signal during which own voice detection module 308 indicates that the user is speaking. Based on the environmental noise level being below a threshold, an entirety of the audio signal during those portions may be considered own voice content. Additionally or alternatively, the own voice content may be extracted from the audio signal based on the environmental noise data, such as by canceling the environmental noise data and/or filtering the environmental noise data. Additionally or alternatively, biomarker feature analysis module 314 may receive own voice content extracted from the audio signal (e.g., by classifier 310).

Biomarker feature analysis module 314 may apply any suitable biomarker feature analysis to the own voice content. For example, biomarker feature analysis module 314 may extract biomarker features from the own voice content, analyze the biomarker features for early signs of neurodegenerative disorders, and output diagnosis data 316. Diagnosis data 316 may include any data indicative of whether the user is presenting any such early signs of neurodegenerative disorders.

While hearing device 302 is shown to include specific modules, other example embodiments may omit modules, combine modules and/or include different modules may perform different portions of described functionality.

Figure 4:
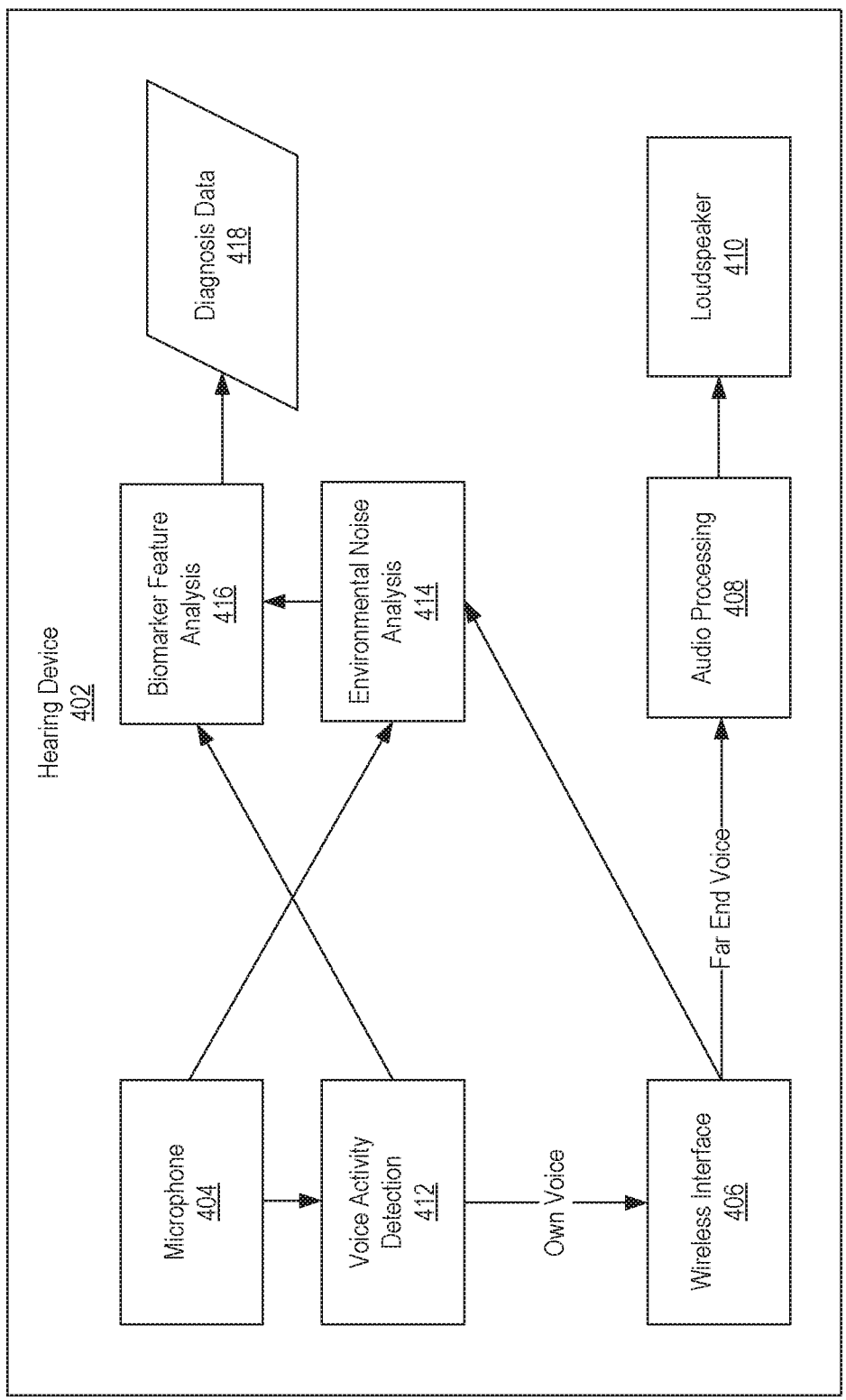

FIG. 4 illustrates another exemplary hearing device 402 including biomarker analysis. Hearing device 402 may be an implementation of hearing device 100 that includes an implementation of configuration 200. For instance, hearing device 402 includes a microphone 404 (e.g., an implementation of microphone 106). Hearing device 402 further includes a wireless interface 406, an audio processing module 408, a loudspeaker 410, a voice activity detection module 412, an environmental noise analysis module 414, and a biomarker feature analysis module 416.

Wireless interface 406 may be configured to wirelessly communicate with other devices, such as a mobile phone, a tablet, a computer, or any other device including a processor and a wireless interface. Such communication with other devices may provide additional information and/or context to hearing device 402 for determining own voice content and environmental noise content. Wireless interface 406 may be implemented in any suitable manner, such as a Bluetooth interface, a near field communication interface, or any other suitable interface configured to operate in accordance with any suitable wireless protocol.

For example, hearing device 402 may communicate with a smartphone to enable a user of hearing device 402 to have phone conversations via hearing device 402. Generally during a phone conversation, the user may alternate dialogue with a person on a far end of the phone conversation. Audio received by the smartphone from the person on the far end may be transmitted to hearing device 402 via wireless interface 406. Hearing device 402 may receive such far end voice content and process the far end voice content with audio processing module 408 (e.g., implemented in any suitable manner). Audio processing module 408 may provide processed audio to loudspeaker 410 (e.g., an implementation of output transducer 108) to provide the audio content to the user.

As far end voice content is received directly via wireless interface 406, speech content in an audio signal detected by microphone 404 may be considered likely to be own voice content. Hearing device 402 may detect a voice in the audio signal via voice activity detection module 412 (e.g., implemented by any combination of own voice sensors 306, own voice detection module 308, classifier 310, or any other suitable manner). Further, a volume of the voice detected and/or a relative volume of the voice to an environmental noise level may provide additional indication whether the voice is own voice content. Hearing device may provide the own voice content to wireless interface 406 to transmit to the person on the other end of the phone conversation. Additionally or alternatively, hearing device 402 may receive own voice content from the smartphone (e.g., detected by a microphone on the smartphone) via wireless interface 406. Hearing device 402 may compare own voice content received from the smartphone with own voice content detected in the audio signal and/or use the own voice content received from the smartphone to enhance or augment the own voice content detected in the audio signal.

Environmental noise analysis module 414 may analyze environmental noise in a manner similar to environmental noise analysis module 312. Additionally, however, environmental noise analysis module 414 may receive information via wireless interface 406 that indicates portions of the audio signal detected by microphone 404 in which own voice content is absent (e.g., when wireless interface 406 is receiving incoming voice content in a phone conversation environment). Alternatively, environmental noise analysis module 414 may directly receive such portions of the audio signal in which own voice content is absent, as such portions of the audio signal may be considered entirely or substantially environmental noise content.

Biomarker feature analysis module 416 (e.g., an implementation of biomarker feature analysis module 314) may receive own voice content from voice activity detection module 412 and environmental noise data from environmental noise analysis module 414 to apply biomarker feature analysis and output diagnosis data 418, which may include any data indicative of whether the user presents any early signs of neurodegenerative disorders.

Hearing device 402 may receive other any other suitable information via wireless interface 406 that provides additional context for own voice content and/or environmental noise content. As another example, hearing device 402 may be communicatively coupled via wireless interface 406 with a device (e.g., a mobile phone) that includes an application that enables a user to record and/or present the user's voice for biomarker feature analysis. For instance, hearing device 402 may include a biomarker feature analysis mode, in which hearing device 402 presents to the user via the application on the device instructions to provide specific types of audio content. For example, hearing device 402 may instruct the user to present a sample of environmental noise content for a first portion of time. Hearing device 402 may determine based on the environmental noise content whether a level of the environmental noise is below a threshold. Based on such a determination, hearing device 402 may then instruct the user to provide own voice content. For instance, hearing device 402 may provide, via the application on the device, a set of words for the user to read aloud. The own voice content may be detected by microphone 404 and/or received via a microphone on the device. Hearing device 402 may then apply biomarker feature analysis heuristics to the own voice content as described herein. As an additional example, hearing device 402 may be communicatively coupled to a device (e.g., a mobile phone) that includes a push-to-talk over cellular feature. The push-to-talk feature may enable the device to operate in a fashion similar to a walkie-talkie, allowing the user to push (and/or push and hold) a button to configure the device between a voice reception mode and a transmit mode. The push-to-talk feature may provide additional context, as the user is likely providing own voice content during the transmit mode. Further, environmental noise may be analyzed during the voice reception mode. Based on such information, hearing device 402 may detect own voice content and apply biomarker feature analysis heuristics as described herein.

Figure 5:
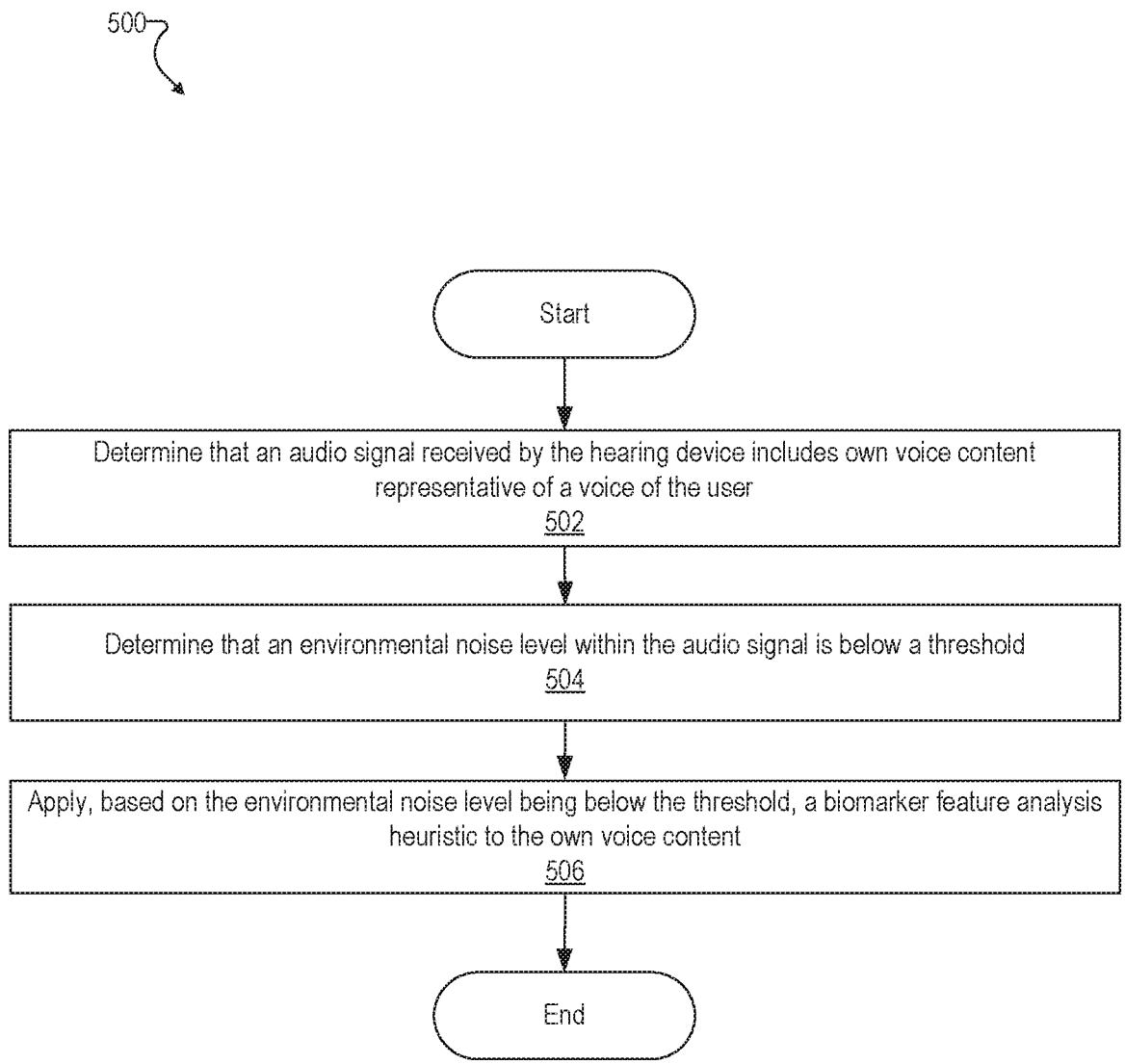
FIG. 5 illustrates an exemplary method for biomarker analysis on a hearing device according to principles described herein.

FIG. 5 illustrates an exemplary method 500. One or more of the operations shown in FIG. 5 may be performed by any of the hearing devices described herein. While FIG. 5 illustrates exemplary operations according to one embodiment, other embodiments may omit, add to, reorder, and/or modify any of the operations shown in FIG. 5.

In operation 502, a hearing device configured to be worn by a user determines that an audio signal received by the hearing device includes own voice content representative of a voice of the user. Operation 502 may be performed in any of the ways described herein.

In operation 504, the hearing device determines that an environmental noise level within the audio signal is below a threshold. Operation 504 may be performed in any of the ways described herein.

In operation 506, the hearing device applies, based on the environmental noise level being below the threshold, a biomarker feature analysis heuristic to the own voice content. Operation 506 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A hearing device configured to be worn by a user, the hearing device comprising:
   a microphone configured to detect an audio signal;
   a processor communicatively coupled to the microphone and configured to:
      determine that the audio signal includes own voice content representative of a voice of the user;
      determine that an environmental noise level within the audio signal is below an environmental noise level-related threshold; and
      apply, based on the determining that the environmental noise level is below the environmental noise level-related threshold, a biomarker feature analysis heuristic to the own voice content.

2. The hearing device of claim 1, wherein:
   the determining that the audio signal includes the own voice content includes determining that the own voice content is present during a first portion of the audio signal and absent during a second portion of the audio signal; and
   the determining that the environmental noise level within the audio signal is below the environmental noise level-related threshold includes measuring the environmental noise level within the audio signal during the second portion of the audio signal.

3. The hearing device of claim 2, further comprising a wireless interface configured to receive incoming voice data from a phone in a voice reception mode and transmit the own voice content to the phone in a transmission mode, and wherein:
   the phone is configured to operate in a push-to-talk mode, in which the user selects between the voice reception mode and the transmission mode;
   the first portion of the audio signal is detected during the transmission mode; and
   the second portion of the audio signal is detected during the voice reception mode.

4. The hearing device of claim 2, further comprising a wireless interface configured to receive incoming voice data from a phone and transmit the own voice content to the phone, and wherein:
   the determining that the own voice content is absent during the second portion of the audio signal includes receiving the incoming voice data during the second portion of the audio signal.

5. The hearing device of claim 4, wherein the determining that the audio signal includes own voice content includes receiving additional own voice content from the phone.

6. The hearing device of claim 1, wherein:
   the determining that the audio signal includes the own voice content includes determining that the own voice content is present during a first portion of the audio signal and absent during a second portion of the audio signal; and the determining that the environmental noise level within the audio signal is below the environmental noise level-related threshold includes:
analyzing a sample of the environmental noise, and canceling, based on the sample, the environmental noise.

7. The hearing device of claim 1, wherein:
the determining that the audio signal includes the own voice content includes determining that the own voice content is present during a first portion of the audio signal and absent during a second portion of the audio signal; and
the determining that the environmental noise level within the audio signal is below the environmental noise level-related threshold includes filtering the environmental noise from the audio signal.

8. The hearing device of claim 1, wherein the processor is further configured to provide a biomarker feature analysis mode including a first specified portion of time in which the user may provide a sample of the environmental noise and a second specified portion of time in which the user may provide the own voice content.

9. The hearing device of claim 1, wherein the determining that the audio signal includes the own voice content includes receiving data from an own voice sensor.

10. The hearing device of claim 9, wherein the own voice sensor includes at least one of a bone conduction microphone and a canal microphone.

11. The hearing device of claim 1, wherein:
the biomarker feature analysis heuristic includes detecting biomarker features for indications for a neurodegenerative disease; and
the processor is further configured to output a result of the biomarker feature analysis heuristic.

12. A hearing device configured to be worn by a user, the hearing device comprising:
a microphone configured to detect an audio signal;
a wireless interface configured to at least one of:
receive incoming voice data from an additional device, and
transmit own voice content representative of a voice of the user to the additional device;
a processor communicatively coupled to the microphone and the wireless interface, the processor configured to:
determine that the audio signal includes the own voice content during a first portion of the audio signal;
determine that the own voice content is absent from the audio signal during a second portion of the audio signal when the wireless interface is receiving the incoming voice data;
determine that an environmental noise level within the second portion of the audio signal is below an environmental noise level-related threshold; and
apply, based on the determining that the environmental noise level is below the environmental noise level-related threshold, a biomarker feature analysis heuristic to the own voice content.

13. A method comprising:
determining, by a hearing device configured to be worn by a user, that an audio signal received by the hearing device includes own voice content representative of a voice of the user;
determining, by the hearing device, that an environmental noise level within the audio signal is below an environmental noise level-related threshold; and
applying, by the hearing device, based on the determining that the environmental noise level is below the environmental noise level-related threshold, a biomarker feature analysis heuristic to the own voice content.

14. The method of claim 13, wherein:
the determining that the audio signal includes the own voice content includes determining that the own voice content is present during a first portion of the audio signal and absent during a second portion of the audio signal; and
the determining that the environmental noise level within the audio signal is below the environmental noise level-related threshold includes measuring the environmental noise level within the audio signal during the second portion of the audio signal.

15. The method of claim 14, further comprising:
receiving, by the hearing device, incoming voice data from a phone communicatively coupled to the hearing device; and
transmitting, by the hearing device, the own voice content to the phone;
wherein the determining that the own voice content is absent during the second portion of the audio signal includes receiving the incoming voice data during the second portion of the audio signal.

16. The method of claim 13, wherein:
the determining that the audio signal includes the own voice content includes determining that the own voice content is present during a first portion of the audio signal and absent during a second portion of the audio signal; and
the determining that the environmental noise level within the audio signal is below the environmental noise level-related threshold includes:
analyzing a sample of the environmental noise, and
canceling, based on the sample, the environmental noise.

17. The method of claim 13, further comprising:
providing a biomarker feature analysis mode including a first specified portion of time in which the user may provide a sample of the environmental noise and a second specified portion of time in which the user may provide the own voice content.

18. The method of claim 13, wherein the determining that the audio signal includes the own voice content includes receiving data from an own voice sensor of the hearing device.

19. The method of claim 18, wherein the own voice sensor includes at least one of a bone conduction microphone and a canal microphone.

20. The method of claim 13, wherein the applying the biomarker feature analysis heuristic includes detecting biomarker features for indications for a neurodegenerative disease.

* * * * *